United States Patent
Shaw et al.

(10) Patent No.: US 11,141,531 B2
(45) Date of Patent: Oct. 12, 2021

(54) DENTAL SAFETY SYRINGE

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US)

(73) Assignee: Retractable Technologies, Inc., Little Elm, TX (US)

( * ) Notice: Subject to any disclaimer, the term of this patent is extended or adjusted under 35 U.S.C. 154(b) by 107 days.

(21) Appl. No.: 15/917,208

(22) Filed: Mar. 9, 2018

(65) Prior Publication Data

US 2018/0256819 A1    Sep. 13, 2018

Related U.S. Application Data (60) Provisional application No. 62/469,294, filed on Mar. 9, 2017.

(51) Int. Cl.
*A61M 5/24* (2006.01)
*A61M 5/32* (2006.01)

(52) U.S. Cl.
CPC .......... *A61M 5/24* (2013.01); *A61M 5/3221* (2013.01); *A61M 5/3271* (2013.01); *A61M 2005/3247* (2013.01)

(58) Field of Classification Search
CPC .......... A61M 5/24; A61M 5/28; A61M 5/322; A61M 5/150732; A61M 5/31511; A61M 5/3232; A61M 2005/2477; A61M 5/315; A61M 5/31505; A61M 5/3271; A61M 2005/2403; A61M 2005/2407; A61M 2005/2414; A61M 2005/31508; A61M 5/3129; A61M 5/31501; A61M 5/31515; A61M 5/3221; A61M 5/3272; A61M 5/3276; A61M 5/5066; A61M 2005/323;
(Continued)

(56) References Cited

U.S. PATENT DOCUMENTS 4,744,790 A * 5/1988 Jankowski ............. A61M 5/24
604/232
4,767,413 A * 8/1988 Haber ................... A61M 5/326
604/198
(Continued)

FOREIGN PATENT DOCUMENTS

GB            809773        10/1956

*Primary Examiner* — Bhisma Mehta
*Assistant Examiner* — Larry R. Wilson
(74) *Attorney, Agent, or Firm* — Monty L Ross PLLC; Monty L. Ross (57) ABSTRACT

A dental safety syringe comprising selectively attachable barrel and plunger assemblies, the barrel assembly desirably further comprising a needle cartridge containing a needle holder and spring, and having a distal end from which a needle can be made to project forwardly while administering a medication and then subsequently withdrawn into the needle cartridge to avoid contamination following or between injections. The needle cartridge also comprises a proximal end having a recess into which an ampule containing medication can be inserted prior to connecting the plunger assembly to the barrel assembly so that a rubber dam in the distal end of the ampule is pierced by the proximal end of the needle whenever the syringe is fully assembled.

6 Claims, 9 Drawing Sheets

(58) Field of Classification Search
CPC ...... A61M 2005/3247; A61M 2205/12; A61B 5/150732
See application file for complete search history.

(56) References Cited

U.S. PATENT DOCUMENTS

| | | | | |
|---|---|---|---|---|
| 4,919,657 | A * | 4/1990 | Haber | A61M 5/24 |
| | | | | 604/197 |
| 4,946,446 | A * | 8/1990 | Vadher | A61M 5/3271 |
| | | | | 604/198 |
| 5,232,457 | A | 8/1993 | Grim | |
| 5,338,311 | A * | 8/1994 | Mahurkar | A61M 5/322 |
| | | | | 604/110 |
| 5,997,512 | A | 12/1999 | Shaw | |
| 6,221,055 | B1 | 4/2001 | Shaw | |
| 7,033,343 | B2 * | 4/2006 | McWethy | A61M 5/3257 |
| | | | | 222/327 |
| 2008/0051729 | A1 * | 2/2008 | Cheng | A61M 5/3272 |
| | | | | 604/232 |

* cited by examiner

DENTAL SAFETY SYRINGE

1. FIELD OF THE INVENTION

This invention relates to a dental safety syringe having a barrel assembly and a plunger assembly that can be selectively and releasably interconnected. The barrel assembly is configured to receive and support a needle cartridge containing a needle holder, needle and a distal end through which the needle is made to project forwardly for administering a medication and is then subsequently withdrawn into the needle cartridge to avoid contamination between injections or following treatment. The plunger assembly is configured to receive and support a prefilled ampule containing local anesthesia or another medicinal fluid. When the barrel assembly and the plunger assembly are slidably engaged and interconnected as disclosed herein, a fluid flow path is established between the interior of the ampule and the distal end of the needle, and fluid is expelled through the needle by moving a plunger rod forwardly relative to the ampule, needle cartridge and barrel. One aspect of the invention relates to a dental safety syringe having a needle holder that is rearwardly biased inside the needle cartridge when the needle projects forwardly from the barrel. Another aspect of the invention relates to a needle holder having a proximal end that is configured to receive and place a distal end of the ampule in fluid communication with a proximal end of the needle. Another aspect of the invention relates to a twist-lock mechanism that influences and limits sliding engagement between the barrel assembly and plunger assembly during use of the subject dental safety syringe. As used throughout this disclosure, "distal" refers to an end portion that is forwardly facing and nearer to the patient and "proximal" refers to an end portion that is rearwardly facing and nearer to the user. Following a treatment, the needle cartridge can be removed from the syringe and disposed of in any clinically acceptable manner, and the barrel and plunger can be autoclaved or otherwise sterilized for reuse.

2. DESCRIPTION OF RELATED ART

Dental syringes comprising barrel assemblies and plunger assemblies are well known. The syringe barrel and plunger are often configured for use with ampules containing medications that are injectable into the mouth or gums of a patient. Dentists often inject a first quantity of a medication such as a local anesthetic, and then lay the syringe down on a tray until a further injection is needed while treating the same patient. More recently, dental syringes have been developed that comprise mechanisms by which the needle can be temporarily withdrawn back into the syringe until a further injection is needed. However, because of various design factors in such dental syringes, bodily fluids such as blood and saliva can be withdrawn from the patient when the needle is retracted, potentially exposing a dentist or hygienist to pathogenic contamination because the needle is not contained within an enclosure between uses or during removal and disposal subsequent to treatment. Prior art dental syringes are disclosed, for example, in the following United States patents and in other patents cited in them: U.S. Pat. Nos. 5,997,512 and 6,221,055. These patents may also be cited in other patents or published pending applications that may be prior art to the subject application.

SUMMARY OF THE INVENTION

This invention relates to a dental safety syringe comprising cooperatively configured, slidably engageable barrel and plunger assemblies intended for use in administering local anesthesia or another medication to a patient undergoing dental treatment. According to one satisfactory embodiment of the invention, the barrel assembly further comprises a removable needle cartridge containing a needle having oppositely facing beveled needle tips, a needle holder and a biasing element that biases the needle holder rearwardly when the needle is moved to a forwardly projecting position.

According to another embodiment of the invention, the biasing element is a compressible coil spring surrounding a part of the needle and needle holder, and that is seated in the distal end of the barrel. The spring is compressed by rearward movement of the needle holder relative to the barrel and when compressed exerts a rearwardly directed force against an annular shoulder near the proximal end of the needle holder.

According to another embodiment of the invention, the distal end of the needle cartridge has an opening through which the distal end of a needle is advanced to project forwardly from the distal end of the barrel prior to administering a medication and then subsequently withdrawn back into the needle cartridge to avoid accidental needle sticks or possible contamination between injections or at the conclusion of a dental treatment or procedure.

According to another embodiment of the invention, a plunger assembly is provided that comprises a substantially cylindrical body with open proximal and distal ends and a plunger rod slidably insertable into the body. The plunger rod further comprises a centrally disposed, longitudinally extending rod portion, a thumb ring attached to the proximal end, and a harpoon or other similarly effective element or structure attached to the distal end that is suitable for use in engaging and attaching the distal end of the plunger rod to a longitudinally slidable piston-plug disposed in the proximal end of a prefilled ampule.

According to another embodiment of the invention, the proximal end of the needle holder disposed inside the needle cartridge of the invention comprises a receptacle defining a recess that comprises the proximal end of the needle and is configured to receive, engage and support the distal end of an ampule having an elastomeric membrane or dam disposed across the distal end that is pierceable by the proximal end of the needle whenever the syringe is fully assembled. The ampule is desirably prefilled and contains local anesthesia or another medication, and is desirably installed onto the plunger assembly prior to connecting the plunger assembly to the barrel assembly. Such ampules also desirably include a rubber or elastomeric piston-plug disposed in the proximal end of the ampule sidewall that can be engaged by a harpoon tip on the plunger rod of the syringe when the plunger assembly is connected to the barrel assembly of the subject dental safety syringe. The piston-plug in the ampule functions as a fluid seal prior to and during use of the ampule, and is longitudinally slidable inside the sidewall of the ampule as the plunger rod of the plunger assembly is advanced relative to the barrel assembly during an injection. When both a needle cartridge and a prefilled ampule as described above have been inserted into the dental safety syringe of the invention, a fluid path through the syringe is thereby established that permits medication to be injected into a patient whenever the needle is projecting forwardly from the barrel and the plunger rod is moved forwardly relative to the barrel to force medication from the ampule into and through the double-ended needle and into a patient.

According to another embodiment of the invention, a dental safety syringe is disclosed that comprises slidably engageable barrel and plunger body sections that are cooperatively configured to permit relative longitudinal and rotational movement to advance and withdraw the distal end of the needle relative to the barrel. According to one satisfactory embodiment of the invention, projecting lugs or fingers are provided on the barrel that are cooperatively engageable with slots disposed on the outside surface of the body of the plunger. The arrangement of the lugs and slots are desirably configured to produce both longitudinal and rotational movement of the plunger body relative to the barrel that causes the distal end of the needle to project forwardly from the needle cartridge and barrel whenever the plunger body is moved forwardly relative to the barrel and allows the needle to be withdrawn into the needle cartridge and barrel whenever the plunger body is moved rearwardly relative to the barrel.

According to another embodiment of the invention, internally threaded nuts are provided on the external surfaces of the proximal end of the barrel and on the distal end of the plunger body to facilitate manual grasping to initiate and continue relative movement between them during repositioning of the needle and to facilitate manual contact and leverage with the fingertips of the user whenever the plunger rod is advanced relative to the plunger body, barrel and needle during an injection.

BRIEF DESCRIPTION OF THE DRAWINGS

The apparatus of the invention is further described and explained in relation to the following drawings wherein.

DESCRIPTION OF THE PREFERRED EMBODIMENTS

Figure 1:
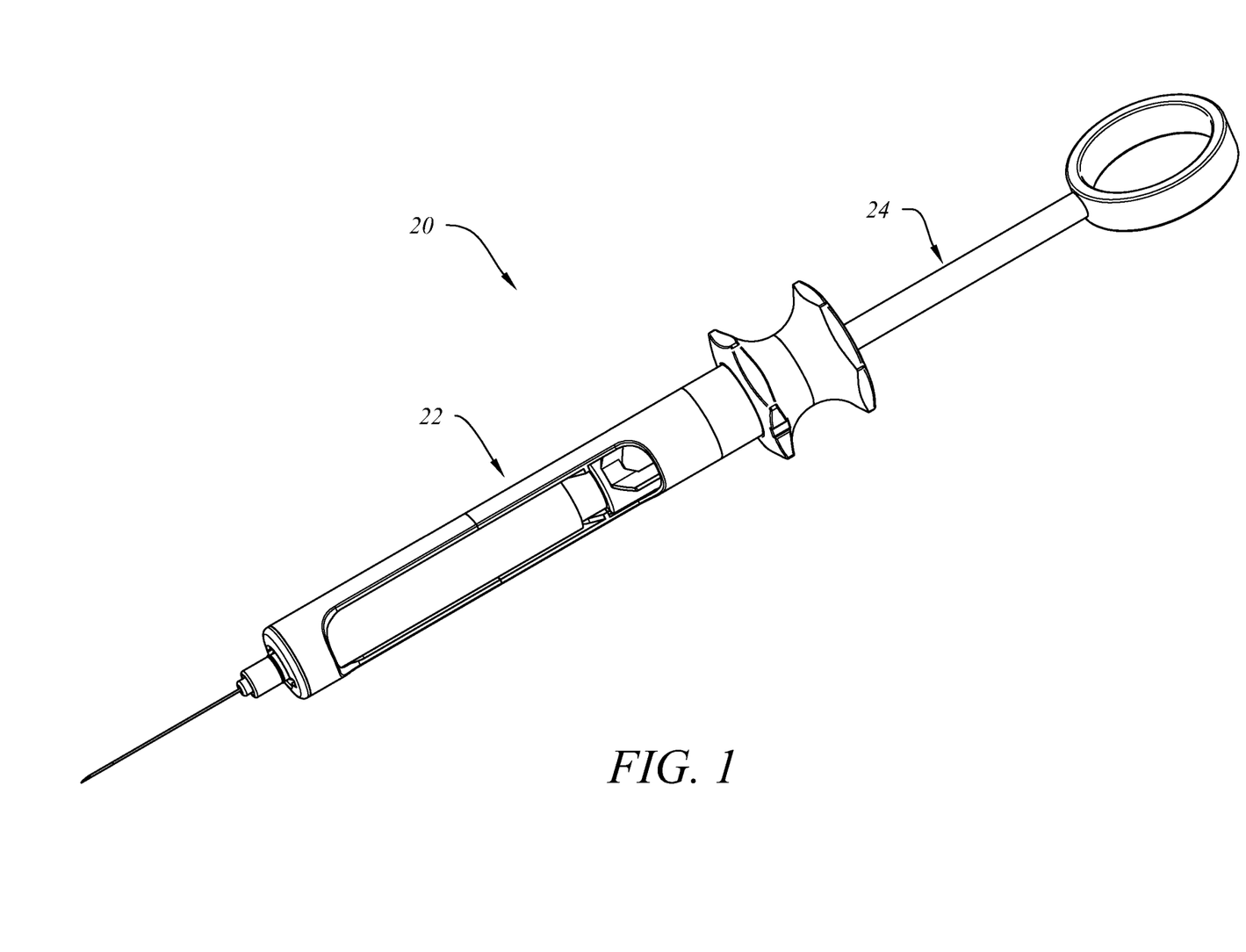
FIG. 1 is a front perspective view of an assembled dental safety syringe configured in accordance with one embodiment of the invention.
Figure 2:
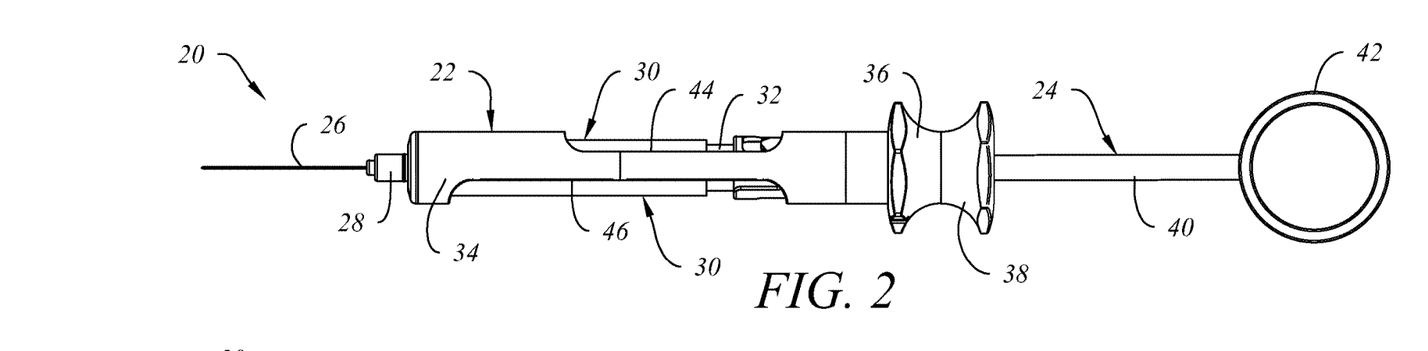
FIG. 2 is a top plan view of the assembled dental syringe of FIG. 1.
Figure 3:
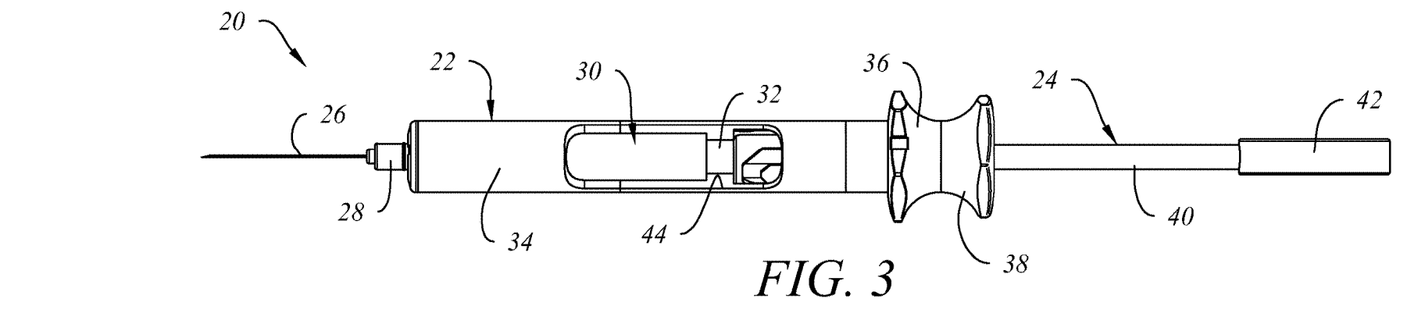
FIG. 3 is a left side elevation view of the assembled dental syringe of FIG. 1.
Figure 4:
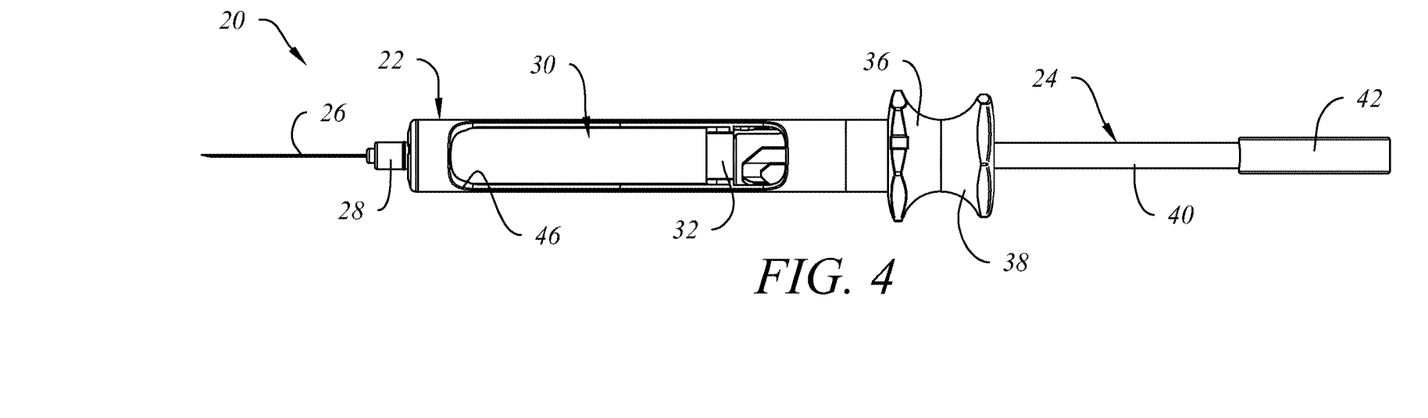
FIG. 4 is a right side elevation view of the assembled dental syringe of FIG. 1.
Figure 5:
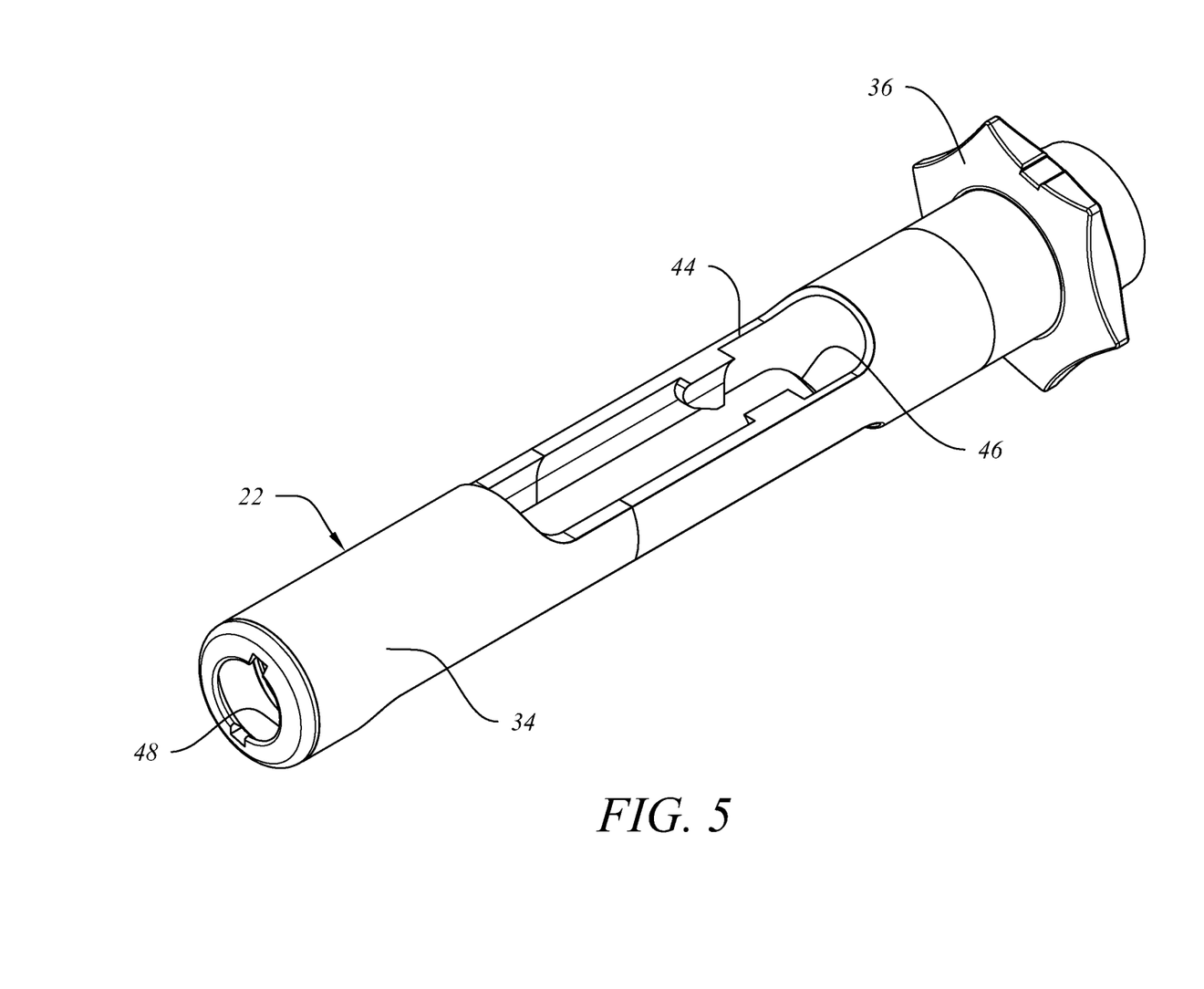
FIG. 5 is an enlarged front perspective view of one embodiment of a barrel suitable for use in a barrel assembly of the invention.
Figure 6:
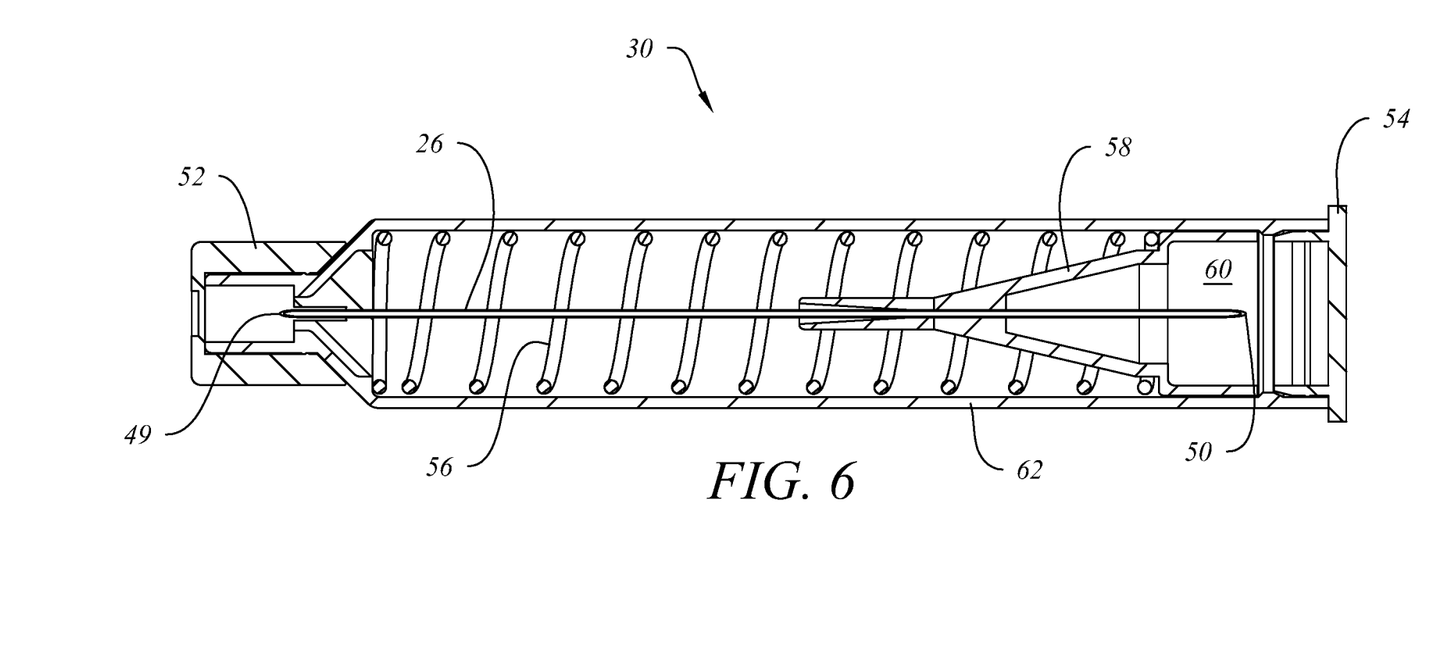
FIG. 6 is a cross-sectional view of one embodiment of a needle cartridge suitable for use in the dental safety syringe of the invention.
Figure 7:
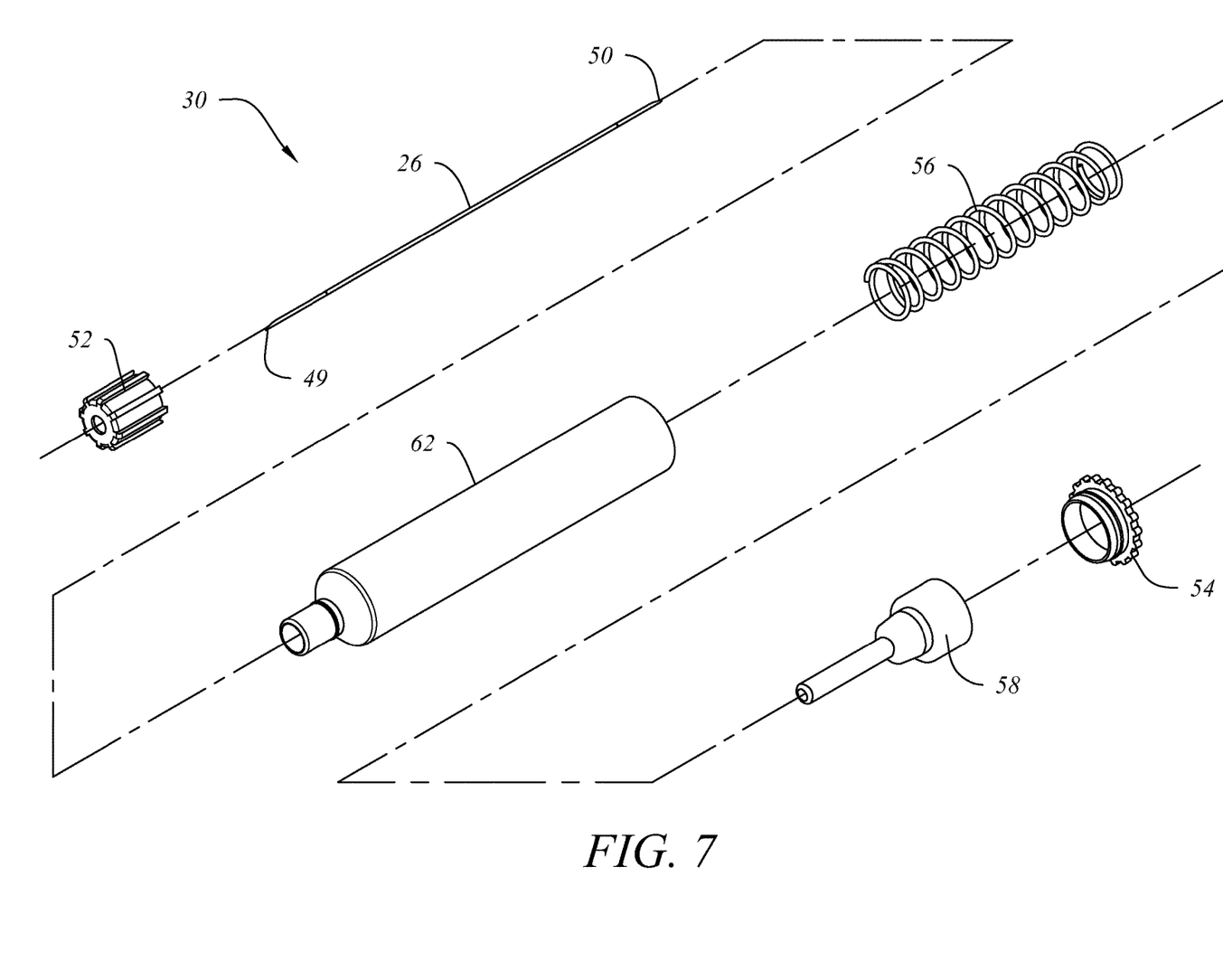
FIG. 7 is an exploded front perspective view of another embodiment of a needle cartridge suitable for use in the dental safety syringe of the invention.

Referring to an embodiment of the invention disclosed in relation to FIGS. 1-5, dental safety syringe 20 comprises barrel assembly 22 and plunger assembly 24. Barrel assembly 22 further comprises substantially cylindrical barrel 34 having longitudinally extending windows 44, 46, with window 44 being shorter than window 46. In FIG. 5, barrel 34 is shown without needle cartridge 30. Needle cartridge 30 is desirably insertable into barrel 34 through window 46 and front end 28 (FIG. 2-4) of needle cartridge housing 62 extends forwardly through opening 48 (FIG. 5) at the front end of barrel 34. When plunger assembly 24 is moved forwardly relative to barrel assembly 22 to the position shown in FIGS. 2-4, needle 26 and the distal tip of needle holder 58 (FIGS. 6 and 7) project forwardly from barrel 34 as discussed below in relation to FIGS. 6-13. Needle 26 is preferably a double-ended needle having beveled tips 49, 50 (see FIG. 6) facing forwardly and rearwardly, respectively. Threaded nuts 36, 38 are desirably provided on barrel assembly 22 and plunger assembly 24, respectively, to provide finger contact surfaces for use as flanges in grasping and moving the two assemblies in relation to each other as needed during assembly and for pulling them apart to initiate withdrawal of needle 26 into needle cartridge 30. Plunger handle rod 40 and thumb ring 42 are desirably provided at the rear of plunger assembly 24 and cooperate with threaded nuts 36, 38 to provide finger contact surfaces for use in moving plunger rod 40 forwardly inside plunger body 64 as discussed below in relation to FIG. 10.

Figure 8:
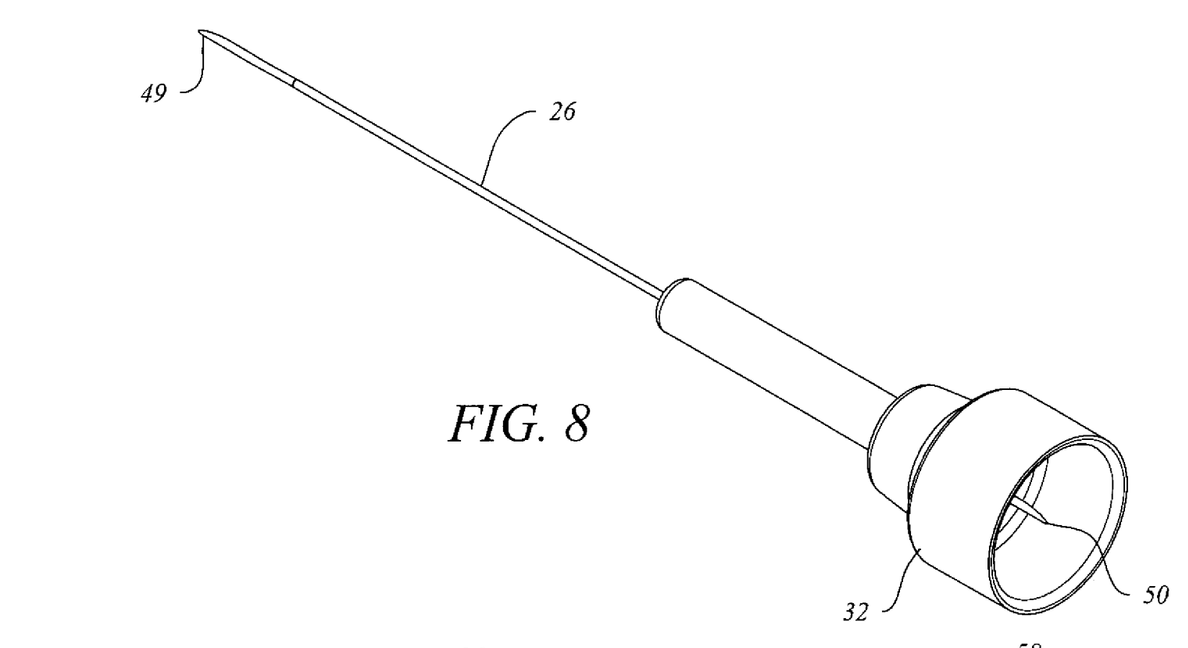
FIG. 8 is a rear perspective view of one embodiment of a needle holder and needle suitable for use in the dental safety syringe of the invention.
Figure 9:
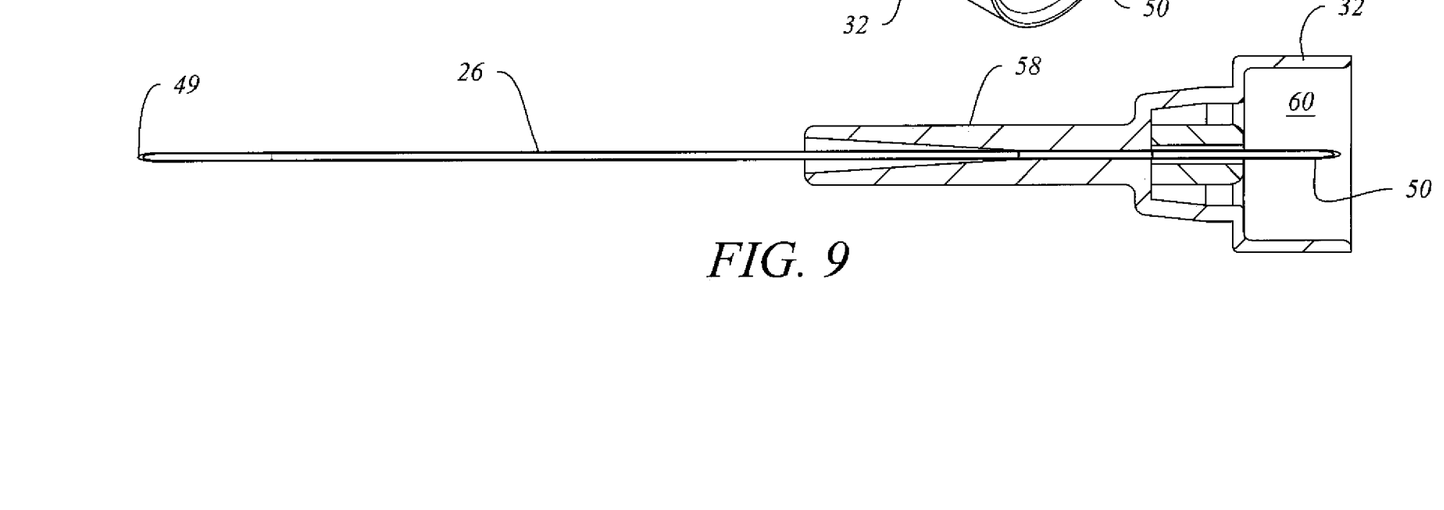
FIG. 9 is a cross-sectional plan view of the needle holder and needle of FIG. 8.

Referring to FIGS. 6-9, needle cartridge 30 satisfactorily further comprises an elongated, substantially cylindrical cartridge housing 62, needle 26 extending through and anchored in longitudinally fixed relation to needle holder 58. Needle holder 58 further comprises a small-diameter through-bore adapted to receive and hold needle 26 in substantially fixed longitudinal relation to needle holder 58 as best seen in FIG. 9. The method attachment of needle 26 inside needle holder 58 is preferably gluing, although other known technologies similarly effective for holding needle 26 in fixed longitudinal relation to needle holder 58 can also be used in making the present invention. The larger-diameter proximal end 32 of needle holder 58 also defines a cylindrical recess 60 configured to receive the distal end of an ampule containing a medicinal fluid prior to use of dental safety syringe 20. Prior to inserting needle cartridge 30 into barrel 34, protective distal cap 52 and proximal cap 54 are desirably removed and can be set aside for possible reuse following removal of needle cartridge 30 from barrel 34 following conclusion of the dental procedure or treatment with which safety dental syringe 20 is being used. Needle cartridge 30 desirably further comprises a biasing element that exerts rearwardly directed pressure against an annular undercut on the larger-diameter section of needle holder 58. As shown in the accompanying drawings, a compressible coil spring 56 is satisfactory for use as the biasing element. Spring 56 is compressed when forwardly directed pressure is applied to plunger assembly 24 and the associated forward movement of plunger assembly 24 relative to barrel assembly 22. Referring specifically to FIGS. 8 and 9, proximal tip 50 of needle 26 is satisfactorily centrally positioned inside cylindrical recess 60 to await insertion through a rubber or otherwise elastomeric and liquid impermeable dam disposed at the distal end of an ampule when inserted into recess 60 as shown in FIG. 12.

Figure 10:
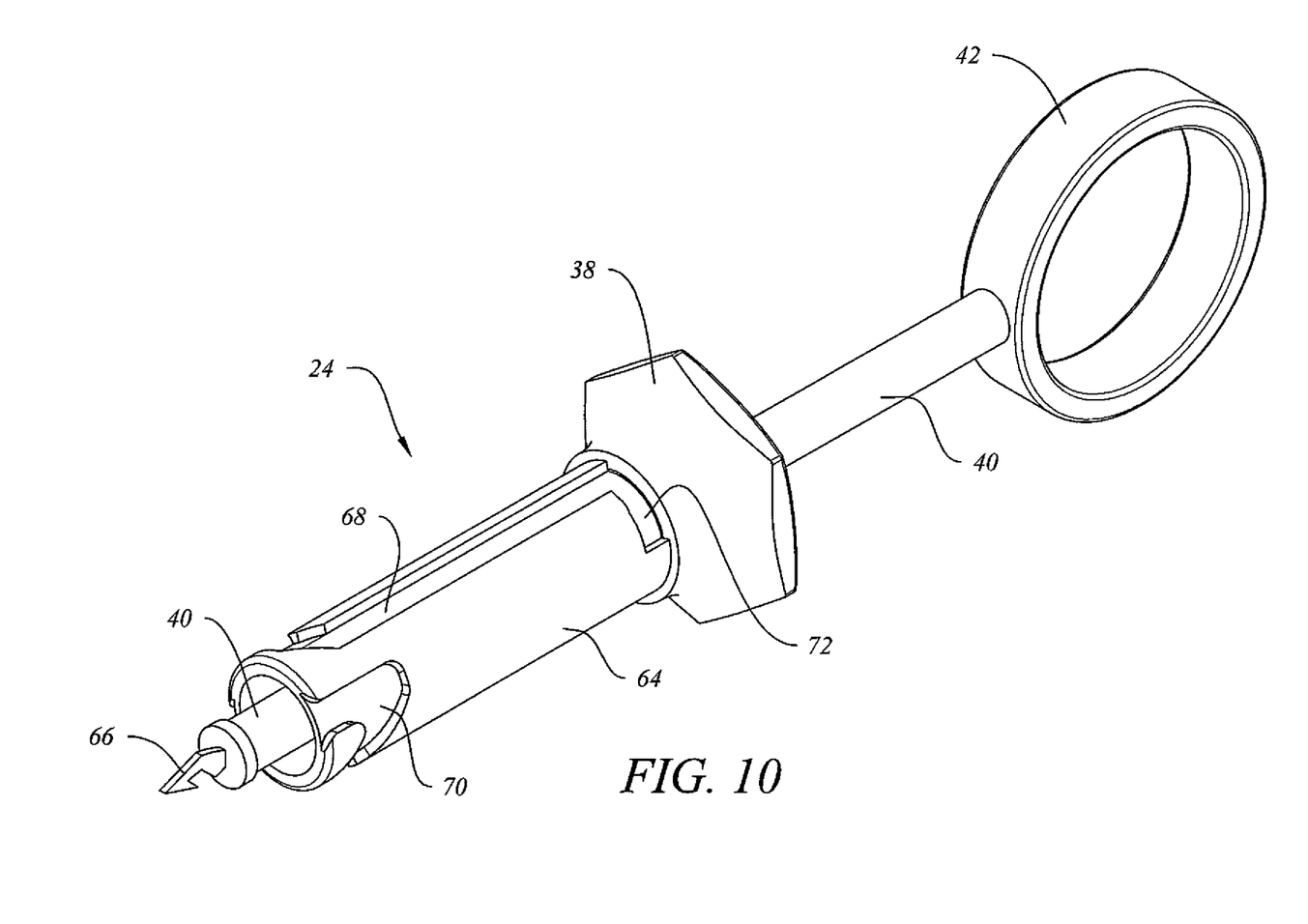
FIG. 10 is a front perspective view of one embodiment of a plunger assembly suitable for use in the dental safety syringe of the invention.

Referring to FIG. 10, one satisfactory embodiment of plunger assembly 24 of the invention further comprises plunger rod 40 that is movable in both the longitudinal and rotational directions relative to plunger body 64. As depicted, plunger rod 40 has thumb ring 42 attached to the proximal end and harpoon 66 attached to the distal end. Harpoon 66 is desirably configured to penetrate into and engage piston-plug 67 disposed in the proximal end of ampule 74. Nut 38 is desirably internally threaded for attachment to a cooperatively threaded outside surface portion at the proximal end of plunger body 64 to facilitate manual movement of plunger assembly 24 relative to barrel assembly 22 (FIG. 1) during assembly of dental safety syringe 20, movement of plunger body 64 relative to barrel 34, movement of plunger rod 40 relative to plunger body 64, and disassembly of plunger assembly 24 from barrel assembly 22. Referring to FIGS. 10-11 and 13-14, slots 68, 70, 72 are desirably provided to act as guides for cooperatively sized and configured lugs 78 disposed on barrel 34 to facilitate, limit and control both longitudinal and rotational movement of plunger body 64 relative to barrel 34 for at least the following purposes: Longitudinally engaging needle cartridge 30 as discussed above; causing the proximal end of needle 26 to pierce the membrane or dam at distal end 76 of ampule 74 (seen in FIG. 11); causing compressible spring 56 to compress; causing needle holder 58 to move forwardly through opening 48 at the distal end of barrel 34 to project forwardly into a use position; and, after injection, causing plunger body 64 to move rearwardly relative to barrel 34 to allow expansion of compressed spring 56, rearward movement of needle holder 58 inside needle cartridge 30, withdrawal of needle 26 into needle cartridge 30, and separation of plunger assembly 24 from barrel assembly 22 at the conclusion of the treatment or procedure for removal and safe disposal of needle cartridge 30 and ampule 74.

Figure 11:
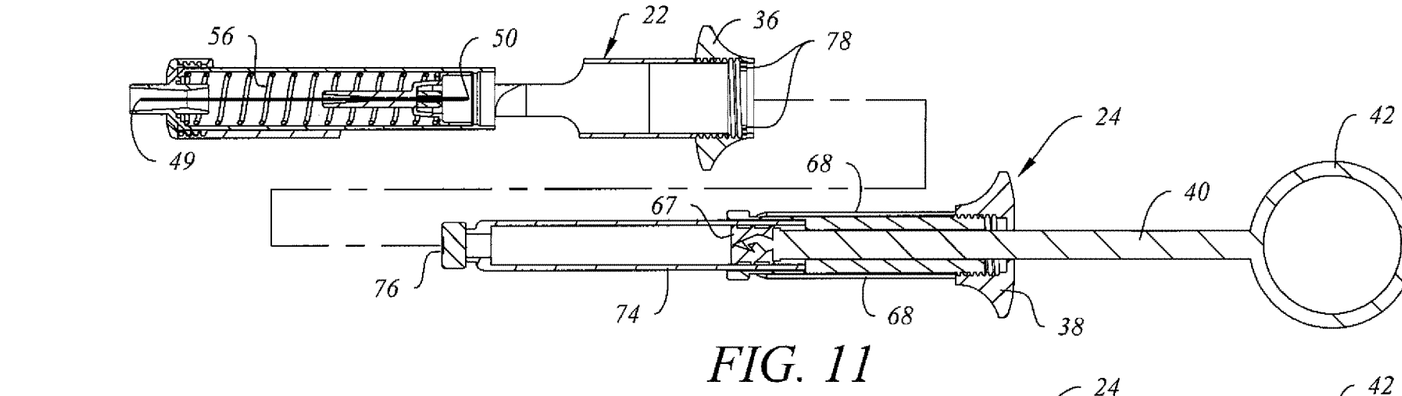
FIG. 11 is a longitudinal cross-sectional view of a barrel assembly and plunger assembly shown together with an ampule prior to assembling one embodiment of the dental safety syringe of the invention.
Figures 12, 13:
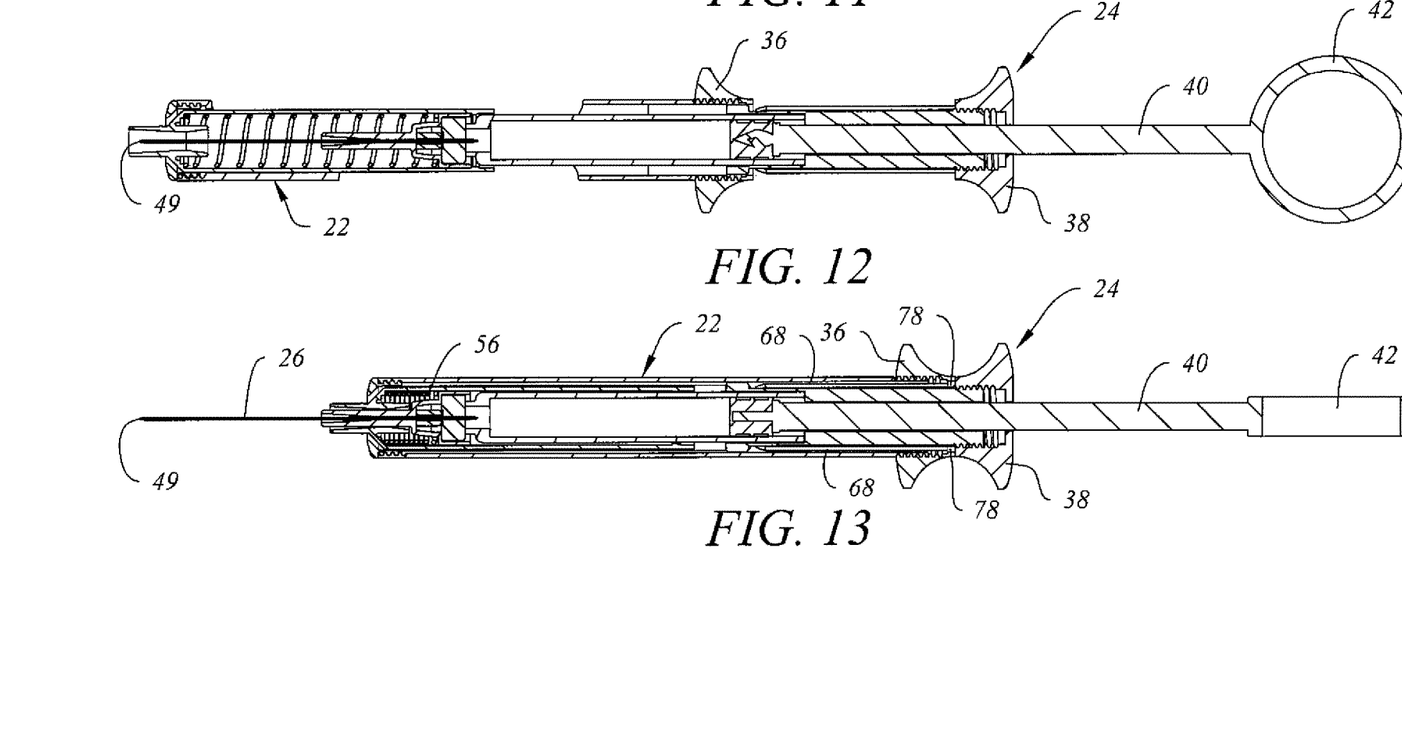
FIG. 12 is a longitudinal cross-sectional view of an assembled embodiment of a dental safety syringe of the invention with the needle disposed inside the needle cartridge of the invention and the plunger rod not yet advanced forwardly to inject fluid through the needle.
FIG. 13 is a longitudinal cross-sectional view of an assembled embodiment of a dental safety syringe of the invention as in FIG. 12 with the spring compressed, the needle projecting forwardly from the needle cartridge of the invention and the plunger rod not yet advanced forwardly to inject fluid through the needle.
Figure 14:
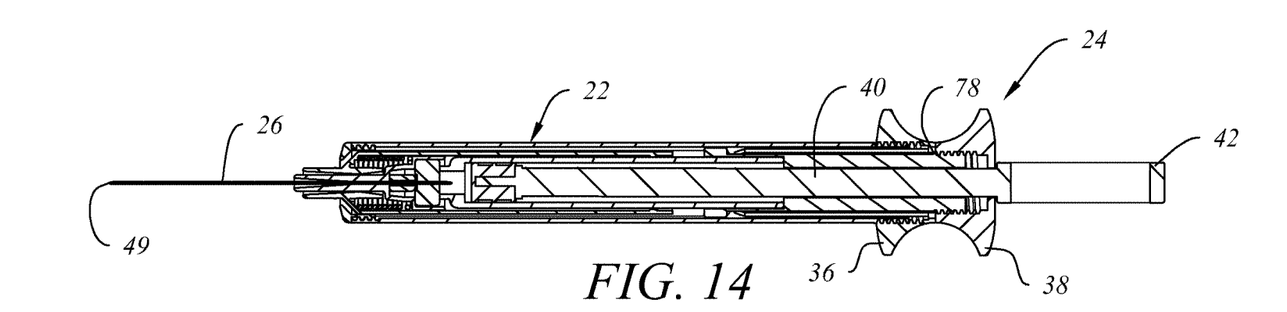
FIG. 14 is a longitudinal cross-sectional view of an assembled embodiment of a dental safety syringe of the invention as in FIG. 13 with the spring compressed and the needle projecting forwardly from the needle cartridge of the invention, but with the plunger rod advanced forwardly as it would be following an injection of substantially all the fluid from inside the ampule.
Figure 15:
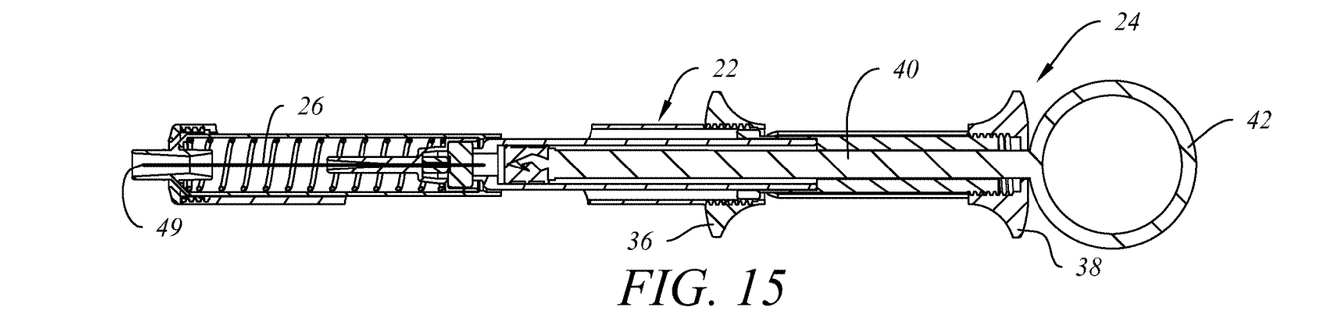
FIG. 15 is a longitudinal cross-sectional view of an assembled embodiment of a dental safety syringe of the invention as in FIG. 14 but with the spring released by rearward movement of the plunger body relative to the barrel and the needle withdrawn back inside the needle cartridge of the invention.
Figure 16:
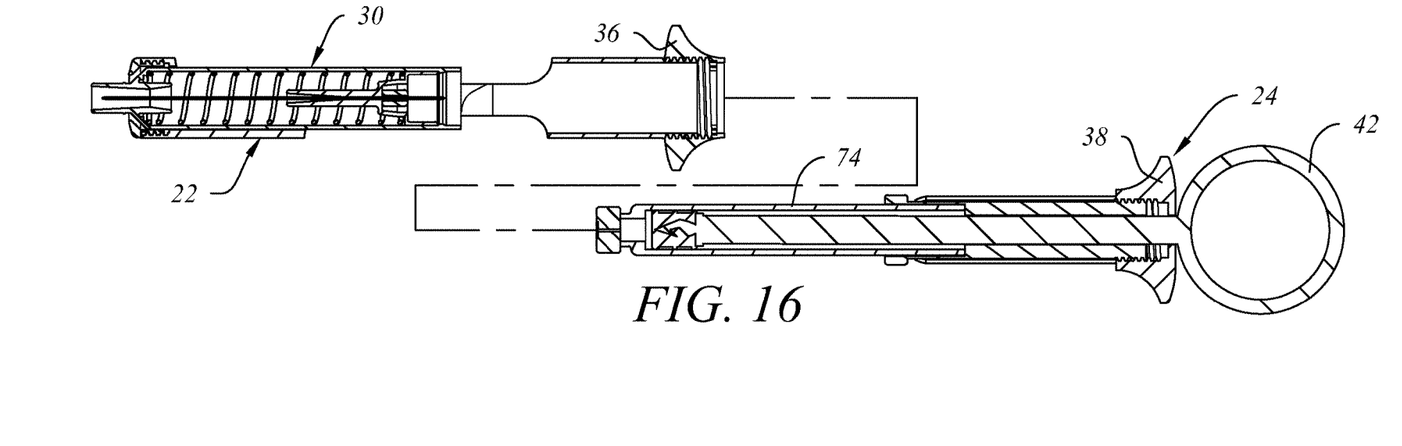
FIG. 16 is a cross-sectional plan view of the dental safety syringe of FIG. 15 as in FIG. 11 with the needle withdrawn and the barrel assembly and plunger assembly disassembled for disposal of the needle cartridge and, upon subsequent separation of the ampule from the harpoon of the plunger rod, safe disposal of both the needle cartridge and the ampule.

The structure and operation of the subject plunger assembly 24 relative to barrel assembly 22 is further described and explained in relation to FIGS. 11-16. Referring to FIG. 11, needle tips 49, 50 are both disposed inside needle cartridge 30 and compression spring 56 is expanded. Ampule 74 is inserted into the distal end of barrel 34 and the piston-plug 67 at the proximal end of ampule 74 is engaged with harpoon 66 of plunger rod 40 as described above, but plunger assembly 24 is not yet connected to barrel assembly 22. Plunger rod 40 is also disposed rearwardly relative to plunger body 64. Referring to FIG. 12, plunger assembly 24 is connected to barrel assembly 22 by inserting distal end 76 of ampule 74 into needle cartridge 30 so that proximal needle tip 50 has pierced the membrane at distal end 76 of ampule 74. Referring to FIG. 13, plunger body 64 of plunger assembly 24 has been moved forwardly and rotated 90 degrees (as is evident from the rotational repositioning of thumb ring 42) to move the needle holder and needle 26 forwardly, causing distal end 49 of needle 26 to project forwardly into a use position and also causing spring 46 to compress, thereby biasing the needle holder rearwardly inside needle cartridge 30. Referring to FIG. 14, plunger rod 40 has been advanced forwardly relative to ampule 74 so that fluid is injected from needle 26 into a patient. Referring to FIG. 15, plunger body 64 has been oppositely rotated to permit longitudinal movement of plunger body 64 relative to barrel 34 to allow the rearward biasing force of spring 56 to move needle holder 58 rearwardly and withdraw needle tip 49 back inside the distal end of the needle cartridge. Referring to FIG. 16, plunger assembly 24 is again separated from barrel assembly 22 so that needle cartridge 30 and ampule 74 can be removed from the respective assemblies for safe disposal.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventor and/or Applicant are legally entitled.

What is claimed is:
1. A dental safety syringe comprising a barrel assembly and a cooperatively configured plunger assembly slidably engageable with the barrel assembly:
   the barrel assembly further comprising a reusable barrel with a longitudinally extending window and projecting lugs, and a removable needle cartridge insertable into the reusable barrel through the window; and
   the cooperatively configured plunger assembly further comprising a plunger body with open proximal and distal ends, an outside surface and slots disposed on the outside surface, a plunger rod slidably insertable into the plunger body having a proximal end and a distal end, and having a thumb ring attached to the proximal end of the plunger rod and a harpoon attached to the distal end of the plunger rod;
   wherein the removable needle cartridge is disposed forwardly of an ampule containing a medication and further comprises a needle, a needle holder biased rearwardly by a compressible spring disposed inside the removable needle cartridge and a distal end from which the needle can be made to project forwardly while administering the medication from the ampule and then subsequently withdrawn into the removable needle cartridge to avoid contamination following or between injections; and
   wherein the projecting lugs of the reusable barrel of the barrel assembly are cooperatively engageable and alignable with the slots disposed on the outside surface of the plunger body and configured to allow both axial and rotational movement of the plunger body relative to the reusable barrel to move the needle to initiate withdrawal of the needle into the removable needle cartridge and reusable barrel whenever the plunger body is moved rearwardly relative to the reusable barrel.

2. The dental safety syringe of claim 1 wherein the needle holder further comprises a recess in which a distal end of the ampule containing the medication can be placed during attachment of the cooperatively configured plunger assembly to the barrel assembly to establish fluid communication between the ampule and the needle.

3. The dental safety syringe of claim 1 wherein the removable needle cartridge is disposable following use.

4. The dental safety syringe of claim 1 wherein the barrel assembly and the cooperatively configured plunger assembly are cooperatively configured to make the needle project forwardly from a distal end of the reusable barrel when the plunger body is moved forwardly in relation to the reusable barrel.

5. The dental safety syringe of claim 1 wherein the barrel assembly and the cooperatively configured plunger assembly are cooperatively configured so that the entire needle is withdrawn into the removable needle cartridge when the plunger body is moved rearwardly in relation to the reusable barrel.

6. The dental safety syringe of claim 1 wherein a fluid flow path is established through the dental safety syringe that causes medication to flow through the needle and into a patient whenever the plunger rod is pushed forwardly relative to the plunger body and the reusable barrel.

* * * * *